United States Patent [19]

Keck et al.

[11] Patent Number: 4,880,752
[45] Date of Patent: Nov. 14, 1989

[54] DIELECTRIC WAVEGUIDE SENSORS AND THEIR USE IN IMMUNOASSAYS

[75] Inventors: Donald B. Keck, Big Flats; Walter F. Love, Horseheads, both of N.Y.

[73] Assignee: Ciba Corning Diagnostics Corp., Medfield, Mass.

[21] Appl. No.: 298,524

[22] Filed: Feb. 24, 1989

Related U.S. Application Data

[63] Continuation of Ser. No. 85,423, Aug. 13, 1987, abandoned, which is a continuation of Ser. No. 773,074, Sep. 6, 1985, abandoned, which is a continuation-in-part of Ser. No. 652,714, Sep. 21, 1984, abandoned.

[51] Int. Cl.$^4$ .................... G01N 21/64; G01N 33/535
[52] U.S. Cl. ................................. 435/7; 250/458.1; 422/57; 422/58; 422/59; 422/68; 435/288; 435/291; 435/808; 436/518; 436/524; 436/528; 436/527; 436/172; 436/805; 436/807; 356/317; 350/96.32; 350/96.33

[58] Field of Search ............... 356/300, 319, 445, 317, 356/318, 417; 250/458.1, 459.1, 461.1, 461.2, 227; 350/96.29, 96.33, 96.32; 436/527, 535, 805, 807, 172; 422/57–59, 68; 435/7, 288, 291, 808

[56] References Cited

U.S. PATENT DOCUMENTS

| | | | |
|---|---|---|---|
| 3,998,591 | 12/1976 | Eckfeldt | 356/445 |
| 4,040,749 | 8/1977 | David et al. | 250/227 |
| 4,050,895 | 9/1977 | Hardy et al. | 250/227 |
| 4,363,533 | 12/1982 | Stowe et al. | 350/96.33 |
| 4,560,248 | 12/1985 | Cramp et al. | 356/412 |

OTHER PUBLICATIONS

Yeh et al, Topical Meeting on Integrated & Guided Waves Optics, Salt Lake City, Utah, Jan. 16–18, 1978, WD7-1 to WD7-4.

Primary Examiner—F. L. Evans
Attorney, Agent, or Firm—William G. Gosz

[57] ABSTRACT

The present invention relates to novel dielectric waveguide (i.e., fiber optic) sensors for use in spectrophotometric assays of analytes in fluids. More particularly, the use of these sensors in immunoassays is disclosed.

22 Claims, 1 Drawing Sheet

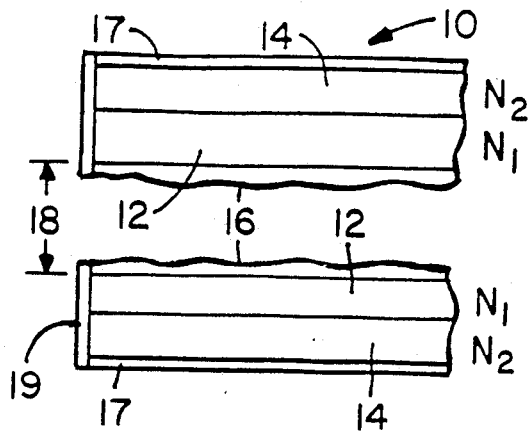
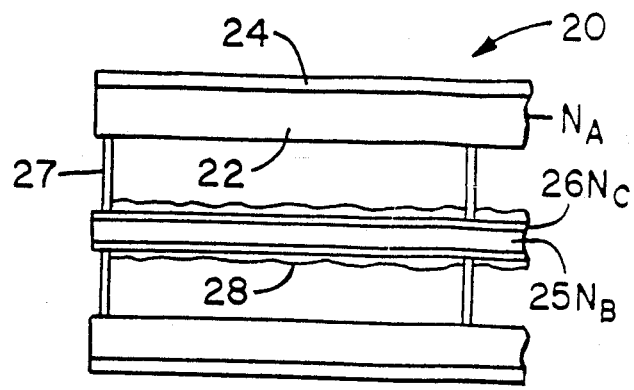
Fig. 1
Fig. 2
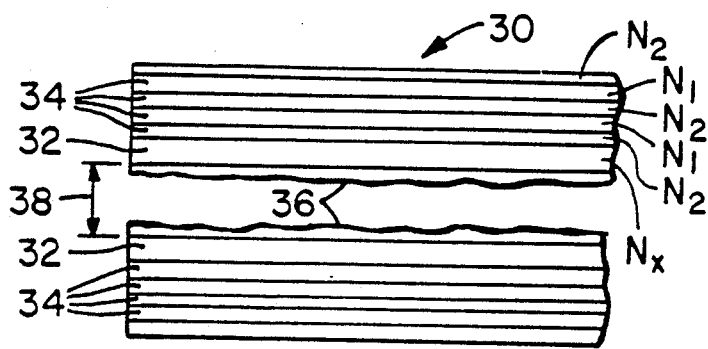
Fig. 3
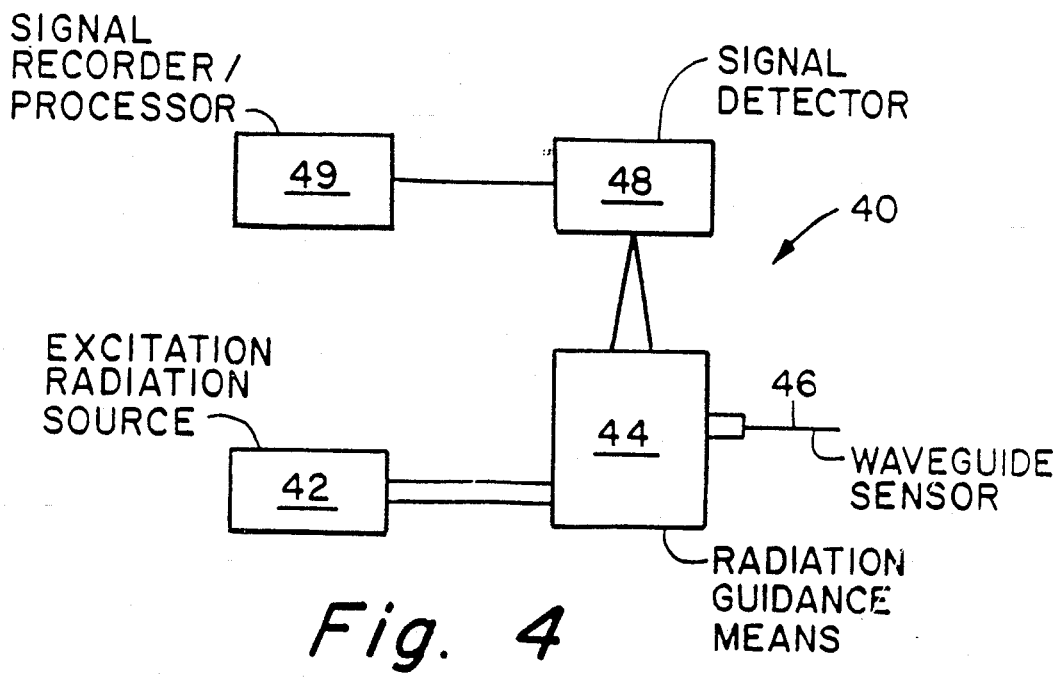
Fig. 4

DIELECTRIC WAVEGUIDE SENSORS AND THEIR USE IN IMMUNOASSAYS

RELATED APPLICATIONS

The present invention is a continuation of Ser. No. 085,423, filed Aug. 13, 1987, now abandoned, which is a continuation of Ser. No. 773,074, filed Sept. 6, 1985, now abandoned, which is a continuation-in-part of Ser. No. 652,714, filed Sept. 21, 1984, now abandoned.

TECHNICAL FIELD

The present invention relates to novel dielectric waveguide (i.e., fiber optic) sensors for use in spectrophotometric assays of analytes in fluids. More particularly, the use of these sensors in immunoassays is disclosed.

BACKGROUND ART

Optical waveguides have been used in various analytical test. For example, in an article entitled "Optical Fiber Fluoroprobes in Clinical Analysis", Clin. Chem, 29/9, pp 1968–1682 (1983), Michael J. Sepaniak et al. describe the use of quartz optical fluoroprobes. By incorporating a single fiber within a hypodermic needle, the authors have been able to obtain in vivo measurement of the fluorescence of various therapeutic drug analytes in interstitial body fluids. Sepaniak et al state that their probe must use a laser radiation source as a fluorescence exciter.

One of the fluoroprobe designs uses a capillary action design for sampling. A length of optical fiber is stripped of its protective coating and slid inside a standard glass capillary tube, touching the walls of the capillary tube at random but not extending the whole length of the tube. This assembly is placed within a hypodermic needle.

Immunoassays using optical waveguides have been disclosed in European Patent Applications 82201107.8 and 81810385.5 to Battelle Memorial Institute. The earlier 1981 application discloses a competitive immunoassay using fiber optics. More particularly, a glass single or multimode optical fiber having a core with an index of refraction ($N_1$) and a cladding with an index of refraction ($N_2$), where $N_1 > N_2$, is coated with an antibody ($A_b$) film to form a sensor fiber.

The immunoassay is done in three steps. First the sensor fiber is immersed into a fluid containing an antigen ($A_g$) analyte specific to $A_b$ plus a known amount of fluorescent-labelled $A_g$. A fluorescent coating forms in proportion to the $A_g$ concentration. Then, an excitation radiation is propagated down the sensor fiber core at one end. The immunoassay relies upon "evanescent wave" phenomena, i.e., the electromagnetic field components which extend a short distance into the cladding, to interact with and excite the external $A_b$/tagged $A_g$ complex. Finally, fluorescence from the excited tagged complex is "reinjected" back into the propagated down the core where it is detected at the opposite end of the fiber. The fluorescence may be reflected and emerge from the output end where it can be separated and detected.

In a continuation-in-part application filed in 1982, Battelle describes how to control the penetration of the exciting evanescent wave into the analyte-containing fluid. Here, the index of refraction of the core $N_1$ is greater than that ($N_2$) of the fluid such that the ratio $N_1/N_2$ permits the evanescent wave to penetrate only to the thickness of the $A_b/A_g$ complex. Thinner layers of such a complex are said to require an index of refraction which would eliminate a glass cladding. The second Battelle application includes more types of immunoassay examples using fiber optics, specifically, "sandwich," "limited reagent," "direct," and "sequential saturation" immunoassays.

An immunoassay apparatus developed by T. Hirschfeld is disclosed in U.S. Pat. No. 4,447,546 issued May 8, 1984, which employs total internal reflection at an interface between a solid phase and a fluid phase of lower index of refraction to produce an evanescent wave in the fluid phase. Fluorescence excited by the wave is observed at angles greater than the critical angle, by total reflection within the solid medium. The solid phase is arranged and illuminated to provide multiple total internal reflections at the interface. Typically, the solid phase is in the form of an optical fiber to which is immobilized a component of a complex formed in an immunochemical reaction. A fluorophore is attached to another component of the complex. The fluorescent labeled component may be either the complement to or the analog of the immobilized component, depending upon whether competive or sandwich assay are to be performed. In the case of competitive assays, the labelled component is typically preloaded to the immobilized component in a controlled concentration.

The fiber and the attached constituent of the assay are immersed in a fluid phase sample and the exciting illumination is injected into an input end of the fiber. The evanescent wave is used to excite fluorescence in the fluid phase, and that fluorescence which tunnels back into the solid phase (propagating in direction greater than the critical angle) is detected at the input end of the fiber.

The observed volume of sample is restricted not only by the rapid decay of the evanescent wave as a function of distance from the interface, but by an equally fast decrease with distance of the efficiency of tunneling, the more distant fluorophores not only being less intensely excited and thus fluorescing less, but their radiation is less efficiently coupled into the fiber. Consequently the effective depth of the sensed layer is much reduced compared to the zone observed by total reflection fluorescence alone, the coupling efficiency effectively scaling down the zone.

Multiple total internal reflections in the solid phase allow the illuminating beam to excite repeatedly an evanescent wave, thereby more efficiently coupling the small excitation source to the sample volume. This also increases the amount of sample sensed. The latter is also enhanced by diffusive circulation of the sample past the fiber surface and to which the material being assayed adheres by reaction as it passes. Diffusion makes the actually sampled layer thickness much larger than the thin surface layer.

All of the radiation that tunnels back into the fibers is within the total reflection angle, and is thus trapped within the fiber. The power available from the fluorescence increases with the length of fiber within the fluorescing material. However, the optical throughput of the system (determined by the aperture and the numerical aperture of the fiber) remains constant. The total fluorescent signal coming from the entire surface of the fiber, multiplied by the increase in sample volume due to diffusion, thus becomes available in a very bright spot (that is the cross-section of the fiber in diameter) exiting the fiber at its input end through a restricted angle determined by the critical angle of reflection within the fiber. Such signal is easily collected at high efficiency and throughput when matched to a small detector.

DISCLOSURE OF THE INVENTION

The present invention comprises three novel dielectric waveguide structures that are useful in spectrophotometric assays of analytes in fluid. Also, it comprises novel methods of spectrophotometrically assaying analytes using these novel waveguides.

The first dielectric waveguides have a core, a cladding, and a reactant coating on the core. Of particular interest is that the core has at least an opening in the core material which is exposed to the analyte-containing fluid, and may be hollow throughout. For descriptive purposes, the waveguide comprises a core transmissive to electromagnetic radiation, preferably visible light, having an index of refraction ($N_1$) and an opening in the core. The core thickness is sufficient to propagate the exciting radiation substantially down the core. A cladding with an index of refraction ($N_2$) (which is less than $N_1$) is about the outside of the core. The cladding is thick enough to contain substantially all of the exciting radiation launched below the critical angle of the waveguides, but to permit penetration of the evanescent wave into a reactant coating. Finally, a reactant coating is placed about the core opening which, in the presence of electromagnetic radiation, interacts with the analyte to form a single radiation.

The light propagation in this and the other waveguide structures to be discussed consists of modes with propagation constant, $\beta$, such that $E \approx e^{i e}$, where E is the lightwave electric field amplitude and z the distance along the waveguide. Oscillatory solutions for E, i.e., bound modes, are obtained for $N_2 k < \beta < N_1 k$ where $$k = \frac{2\pi}{\lambda}$$

and is the free space wavelength of the light. Leaky modes for which $N_3 k < \beta < N_2 k$ are also obtained but these generally decay with length z (where $N_3$ is the index of refraction of the fluid surrounding the waveguide). With a suitable combination of spot size and launch angle, the penetration of light into the analyte can be controlled.

For example, if $N_2 = N_3$ for simplicity, then the extension of the electric field into the analyte is given by:

$$E \sim K\nu(\gamma r) \text{ for } r > a$$

where 2a denotes the thickness of the core region, $\gamma$ is the mode number, $\gamma = (N_1^2 k^2 - \beta^2)^{\frac{1}{2}}$, and K is the modified Hankel function. This applies strictly to the case of a concentric circular fiber but may be used approximately here. The mathematical matching of this evanescent electric field to the core mode electric field gives the value of $\gamma$. For the lowest order mode, vis., $\nu = 0$, $$E \sim \frac{e^{-\gamma r}}{r} \text{ for } r > a$$

Thus, the penetration distance of the light into the analyte depends on which in turn depends on $\lambda$ the mode(s) selected by the launch (initial) conditions ($\nu$), the indices of refractions of the waveguide ($N_1$ and $N_2$) and analyte ($N_3$), and the wavelength of the light ($\lambda$).

The above hollow waveguide can be used in the following manner. The coated waveguide is placed in the analyte-containing fluid for a time sufficient for the analyte to interact with the reactant coating and to form an electromagnetically detectable complex or moeity. Then either while the fiber is still in the fluid or after it has been removed, electromagnetic radiation is propagated down the waveguide core so as to irradiate the interacting moeity, which then produces a single radiation. The last step is to detect the resulting signal radiation by monitoring the core of the waveguide. Typically, the waveguide is a fiber having two ends, either one of which can be monitored.

Another novel dielectric waveguide has two concentric fibers. A support fiber with an index of refraction ($N_A$) has an opening therethrough, i.e., is hollow. A second core fiber with an index of refraction ($N_B$) is axially positioned concentric with the support fiber opening. A means for maintaining this axial position is incorporated to form a multi-element dielectric waveguide. The relationships of $N_A/N_B$ depends upon how one intends on using the waveguide in an assay. $N_B$ can be either greater than, equal to, or less than $N_A$. The selection of materials and waveguide design parameters such as thickness, follow principles either known to the art or described above.

There are three general methods of using the multi-element dielectric waveguide. In the first, the exciting radiation is propagated down the core fiber. The evanescent wave from this propagation interacts with either the analyte itself or the combination of analyte and reactant coating on either of the fibers to produce a signal radiation. Either the core or the support fiber can be monitored to detect the signal radiation, however, the detecting waveguide should have an index of refraction equal to or greater than the excitating waveguide.

Another method uses the hollow support waveguide to propagate the excitation radiation. Again, either waveguide can be used for detection, but the detecting waveguide should have an index of refraction equal to or greater than the exciting waveguide.

The third method does not use the waveguide as an exciter. Rather, the analyte-containing fluid is used as the propagating medium for the excitation radiation. Either waveguide is used for detection. Of course, the fluid must be able to propagate the excitation radiation.

The third dielectric waveguide is an elongated member having a series of claddings about a hollow core. Specifically, the core with an index of refraction ($N_x$) has an opening therethrough, i.e., is hollow. A series of claddings with alternating indices of refraction, ($N_2$) followed by ($N_1$) (where $N_2$ is less than $N_1$ and only one of either can equal $N_x$), is positioned about the core. The number and thickness of the claddings is sufficient to enable electromagnetic radiation to propagate within the hollow core. Such configurations are known to the art as Bragg waveguides. The selection materials and design parameters such as thickness, follow principles either known to the art or described above.

For assay purposes, one coats the interior core surface of a Bragg waveguide with a reactant which, in the presence of electromagnetic radiation, interacts with the analyte to form a detectable signal radiation.

The coated Bragg waveguide can be used in an assay in a method similar to the first hollow waveguide; however, the excitation and signal radiation are both launched and carried down the opening of the core fiber rather than the fiber itself.

Of course, an apparatus useful for practicing the above method would include the following elements: an electromagnetic radiation source; a means for guiding the radiation from the source to the interior of the waveguide, where it is propagated; a signal radiation detection means; and a means for guiding the signal radiation from the waveguide, to the detection means. All of these means are conventional and well known to the skilled artisan.

DESCRIPTION OF THE DRAWINGS

FIG. 1 is a cross-sectional view of a hollow waveguide.

FIG. 2 is a cross-sectional view of a multi-element waveguide.

FIG. 3 is a cross-sectional view of a Bragg waveguide.

FIG. 4 is a diagrammatic view of an apparatus for use with the above waveguides.

MODES OF CARRYING OUT THE INVENTION

A preferred embodiment of a hollow waveguide is shown in FIG. 1. The waveguide 10 comprises a hollow glass cylindrical core 12 having an index of refraction $N_1$, an internal core diameter of about 100 microns, and a thickness of about 250 microns. The core is covered on the outside by a glass cladding 14 having an index of refraction $N_2$, where $N_1$, and a thickness of about 250 microns. Those skilled in the art of optical fibers know how to select suitable optically transmissive materials, such as glass or plastic, and how to make such a structure, therefore a detailed description of the various processes is superfluous. However, the following disclosures are given as exemplary references on both multi-mode and single mode waveguide construction: U.S. Pat. No. 3,695,915 to Maurer et al; U.S. Pat. No. 3,711,262 to Keck et al; U.S. Pat. No. 3,775,075 to Keck et al; and U.S. Pat. No. 3,823,995 to Carpenter.

The interior surface of the waveguide core is covered with an immobilized reactant coating 16. The chemical composition of this coating varies according to the type of analyte being detected and the type of signal radiation one is trying to generate. As for analytes suitable for detection with the present waveguides, the main requirement is for the reactant coating to be able to bind the analyte directly. For example, if the analyte is an immunological substance (i.e., antibody, antigen, or hapten), then the reactant coating comprises a complementary immunological substance which is secured to the core yet able to bind to the analyte. Thus, an antigen (Ag) analyte would require a complementary antibody ($A_b$) component to be immobilized to the core as the reactant coating.

Those of skill in the immunoassay art have applied the selective binding property of antibodies to create different types of immunoassays known as "sandwich", "direct", "limited reagent" and "saturation" assays. See U.S. Pat. No. 4,380,580. The skilled artisan would know how to design an immunoassay by selecting the proper immunological substances for a reactant coating that would be suitable for use on the present coated, hollow waveguides.

Signal radiation selection can affect the selection of the reactant coating as well. For example, if chemiluminescent production of a particular signal is desired in an immunoassay, then the reactant coating can comprise an immobilized chemiluminescent precursor or reactant which, in the presence of the analyte, results in the production of this signal. Alternatively, the precursor can be used according to the methods disclosed in U.S. Pat. No. 4,380,580, where the chemiluminescent precursor is attached to either an antibody or an antigen which would react with the coating. These configurations are opposed to immunoassays where, if fluorescence is the signal to be monitored, then the art knows how to apply fluorescent "tags" either to the analyte or to a competitive analyte (or analogue thereof) without affecting the makeup of the reactant coating.

If desired, a mirror coating 17 can be applied to the outside of the cladding. The effect would be to reflect the isotropic signal radiation so as to permit more of the signal to be propagated back down the waveguide. A mirror coating 19 can also be advantageously applied to one end of the waveguide.

The multi-element waveguide is illustrated in FIG. 2. Preferably, the waveguide comprises two spaced fibers. A hollow, cylindrical support fiber 22 having and index of refraction $N_A$, an interior diameter of 1000 microns, and a thickness of 250 microns is coated with a reflective, mirror layer 24. Positioned within the interior of the support fiber is a core fiber 25 having an index of refraction $N_B$ and a thickness of 250 microns, which may have a cladding 26 about the core having an index of refraction $N_C$ and a thickness of 50 microns. $N_B$ is greater than $N_A$ and less than $N_C$ if the core fiber is used for detection. Spacer means 27 comprising at least an annular ring keeps the core fiber axially and concentrically positioned within the length of the hollow support fiber.

Finally, a reactant coating 28 covers the cladding surface of the core fiber. Again, as discussed above, this coating can have variable compositions.

The third Bragg waveguide 30 has a glass hollow cylindrical core 32 with an interior diameter of 1000 microns and an index of refraction $N_x$, surrounded on the outside by a multicomponent cladding 34 and on the inside with a reactant coating 36 similar to the ones described above. The cladding comprises a series of alternating materials having indices of refraction $N_1$ and $N_2$, where $N_2 < N_1$ and only one of either $N_2$ or $N_1$ can equal $N_x$. The cladding thicknesses vary according to the indices of refraction, as mentioned herein.

In general, an apparatus for using these waveguides in spectrophotometric assays 40 has the five elements diagrammatically presented in FIG. 4. They are: an excitation radiation source 42; a means for guiding the excitation radiation 44 to the waveguide 46, either at the core, the cladding, or the hollow interior, where it is propagated; a signal radiation detection means 48; a means for guiding the signal radiation, also 44 from the waveguide to the signal detection means; and, preferably, a recordation and processing means 49 which can collect detection data in a more permanent form.

Most of these elements are standard features on spectrophotometers. For example, the exciter can be either a dye-tunable laser on a tungsten bulb. The guide means can comprise focusing lenses, monochromator gratings, mirrors, and wavelength selective beam splitters. Finally, the detector and recorder can be either a photomultiplier tube or a photo-diode and a microprocessor with storage and display abilities. The design of such an apparatus would be within the skill of an optics artisan.

An important aspect of any apparatus using the present waveguides is the waveguide alignment means.

That is, part of the function of the guiding means is to ensure that the excitation radiation is propagated within the waveguide. Thus, according to known optical principles the waveguide must be properly aligned with this radiation, otherwise bound analyte will not be excited by an evanescent wave of the proper wavelength. More than one gripping arrangement can be used, from as simple as a matching cylindrical guide sheath to as complicated as movable opposing jaws with precision molded grips.

Having described the invention with particular reference to preferred embodiments, it will be obvious to those skilled in the art to which the invention pertain, that, after understanding the invention, various changes and modifications may be made without departing from the spirit and scope of the invention as defined by the appended claims.

We claim:

1. A dielectric waveguide for use in fluorescence assays of an analyte in a fluid, comprising:
    (a) a core having an index of refraction ($N_1$) and an opening in the core;
    (b) a cladding about the core having an index of refraction ($N_2$) which is less than $N_1$; and
    (c) a reactant coating about the opening of the core which comprises an analyte-binder, wherein the core is transmissive to radiation which can excite fluorescence of a fluorescent tag and transmissive to fluorescent radiation from the fluorescent tag.

2. The dielectric waveguide of claim 1 wherein the core has hollow opening throughout its length.

3. The dielectric waveguide of claim 1 wherein the waveguide has a fiber shape with two ends, one of which has a mirror coating.

4. The dielectric waveguide of claim 1 wherein the waveguide has a fiber shape and a mirror coating on cladding.

5. The dielectric waveguide of claim 1 wherein the reactant coating is an immobilized antibody.

6. The dielectric waveguide of claim 1 wherein the reactant coating is an immobilized antigen.

7. The dielectric waveguide of claim 1 wherein the reactant coating is an enzyme.

8. A method of spectrophotometrically assaying an analyte in a fluid comprising:
    (a) contacting the dielectric waveguide of claim 1 with the fluid for a time sufficient for the analyte and the analyte-binder to be able to interact;
    (b) propagating radiation down the waveguide core so as to irradiate the interacting analyte and analyte-binder in the presence of a fluorescent tag;
    (c) detecting the fluorescence radiation resulting from the irradiation of the analyte interaction by monitoring the waveguide.

9. An improved apparatus for spectrophotometrically assaying an analyte in a fluid having a radiation source and a means for detecting fluorescence radiation, the improvement comprising:
    (a) the dielectric waveguide of claim 1;
    (b) a means for guiding radiation from the source, to the waveguide such that it is propagated down the waveguide; and
    (c) a means for guiding the fluorescence signal radiation from the waveguide to the detection means.

10. A multi-element dielectric waveguide for use in fluorescence assays of an analyte in a fluid comprising:
    (a) a support fiber having an index of refraction ($N_A$) and an opening therethrough;
    (b) a second core fiber axially positioned within the support fiber opening and having an index of refraction ($N_B$);
    (c) a means for maintaining the axial position of the core fiber within the support fiber; and
    (d) a reactant coating on the support fiber or on the core fiber which comprises an analyte-binder, wherein the support fiber and the core fiber are transmissive to radiation which can excite fluorescence of a fluorescent tag and transmissive to fluorescent radiation from the fluorescent tag.

11. The dielectric waveguide of claim 10 wherein $N_B$ is greater than $N_A$.

12. The dielectric waveguide of claim 10 wherein $N_B$ is equal to $N_A$.

13. The dielectric waveguide of claim 10 wherein $N_B$ is less than $N_A$.

14. The dielectric waveguide of claim 10 wherein a mirror coating is placed about the outside of support fiber.

15. The dielectric wavegude of claim 10 wherein the core fiber has a cladding on the outside with an index of refraction $N_C$ which is greater than $N_B$.

16. The dielectric waveguide of claim 10 wherein the core fiber has a reactant coating which, in the presence of electromagnetic radiation, interacts with the analyte to form a signal radiation.

17. The dielectric waveguide of claim 10 wherein the support fiber has a reactant coating which, in the presence of electromagnetic radiation, interacts with the analyte to form a signal radiation.

18. A method of spectrophotometrically assaying an analyte in a fluid comprising:
    (a) contacting the dielectric waveguide of claim 10 with the fluid for a time sufficient for the analyte and the analyte-binder to be able to interact;
    (b) propagating radiation down the core fiber so as to irradiate the combination of analyte and analyte-binder in the presence of a fluorescent tag;
    (c) detecting the fluorescence radiation from the irradiated analyte and analyte-binder interaction by monitoring the waveguide.

19. A method of spectrophotometrically assaying an analyte in a fluid comprising:
    (a) contacting the dielectric waveguide of claim 10 with the fluid for a time sufficient for the analyte and the analyte-binder to be able to interact;
    (b) propagating radiation down the support fiber so as to irradiate the combination of analyte and analyte-binder in the presence of a fluorescent tag;
    (c) detecting the fluorescence radiation from the irradiated analyte and analyte-binder interaction by monitoring the waveguide.

20. A method of spectrophotometrically assaying an analyte in a fluid comprising:
    (a) contacting the dielectric waveguide of claim 10 with the fluid for a time sufficient for the analyte and the analyte-binder to be able to interact;
    (b) propagating radiation within the fluid so as to irradiate the combination of analyte and analyte-binder in the presence of a fluorescent tag;
    (c) detecting the fluorescence radiation from the irradiated analyte and reactant interaction by monitoring the waveguide.

21. A dielectric waveguide for use in fluorescence assays of an analyte in a fluid comprising:

(a) a core having an index of refraction ($N_X$) and an opening therethrough;

(b) a series of claddings about the core having alternating indices of refraction ($N_2$) and ($N_1$) where $N_2$ is less than $N_1$ and only one of either can equal $N_X$, and of such a number and configuration so as to enable radiation which can excite the fluorescence of a fluorescent tag to propagate within the core opening and to enable the fluorescent radiation from the fluorescent tag to propagate within the core opening and;

(c) a reactant coating on the core surface which comprises an analyte-binder.

22. A method of spectrophotometrically assaying an analyte comprising:

(a) contacting the dielectric waveguide of claim 21 with the fluid for a time sufficient for the analyte and the analyte-binnder to interact;

(b) propagating radiation down the waveguide so as to irradiate the combination of analyte and analyte-binder in the presence of a fluorescent tag; and (c) detecting the fluorescence radiation resulting from the irradiation of the analyte and analyte-binder interaction by monitoring the fluid.

* * * * *